US00PP08870P

United States Patent [19]

Trees

[11] Patent Number: Plant 8,870

[45] Date of Patent: Aug. 23, 1994

[54] NEW GUINEA IMPATIENS NAMED BSR-195 SALMON

[75] Inventor: Scott C. Trees, Arroyo Grande, Calif.

[73] Assignee: George J. Ball, Inc., West Chicago, Ill.

[21] Appl. No.: 135,544

[22] Filed: Oct. 14, 1993

[51] Int. Cl.[5] ..... A01H 5/00
[52] U.S. Cl. ..... Plt./87.6
[58] Field of Search ..... Plt. 87.6

*Primary Examiner*—James R. Feyrer
*Attorney, Agent, or Firm*—Burns, Doane, Swecker & Mathis

[57] ABSTRACT

A new and distinct New Guinea Impatiens cultivar named BSR-195 Salmon is provided. This new cultivar was the result of a controlled breeding program wherein a plant designated BFP-67 (non-patented in the United States) was pollinated by a plant designated BFP-10 (non-patented in the United States). The new cultivar forms attractive very large somewhat flat salmon blossoms displaying an iridescent appearance combined with a basal branching character and an upright mounded growth habit, and can be readily distinguished from the Charade cultivar (U.S. Plant Pat. No. 7,787).

1 Drawing Sheet

SUMMARY OF THE INVENTION

The present invention comprises a new and distinctive Impatiens plant, botanically known as New Guinea Impatiens, and hereafter referred to by the cultivar name BSR-195 Salmon.

The new cultivar is the product of a planned breeding program. More specifically, the breeding program which resulted in the production of the new cultivar was carried out in a controlled environment during 1990 at Arroyo Grande, Calif., U.S.A. The female parent (i.e., the seed parent) was a plant designated BFP-67 (non-patented in the United States) which exhibits medium pink blossoms with variegated rugose foliage. The male parent (i.e., the pollen parent) was a plant designated BFP-10 (non-patented in the United States) which exhibits large red blossoms with medium green foliage. Each of the parent plants was a proprietary line of Ball FloraPlant. The parentage of the new cultivar can be summarized as follows:

BFP-67×BFP-10.

The seeds resulting from the above pollination were sown and plants were obtained which were physically and biologically different from each other. Selective study resulted in the identification of a single plant of the new cultivar. This plant had large flat salmon blossoms and initially was designated BSR-195.

It was found that the cultivar of the present invention:

(a) exhibits attractive very large salmon blossoms,
(b) exhibits a good basal branching character,
(c) exhibits an upright mounded growth habit, and
(d) exhibits slightly variegated foliage under high light conditions.

Asexual reproduction of the new cultivar by terminal or stem cuttings taken during 1991 at Arroyo Grande, Calif., U.S.A., has demonstrated that the characteristics of the new cultivar as herein described are firmly fixed and are retained through successive generations of such asexual propagation.

The BSR-195 Salmon cultivar has not been observed under all possible environmental conditions to date. Accordingly, it is possible that the phenotype may vary somewhat with variations in the environment, such as temperature, light intensity, and day length.

When the new cultivar of the present invention is compared to the Charade cultivar (U.S. Pat. No. 7,787), it is found that the new variety exhibits a growth habit which is not as compact as the Charade cultivar. The new cultivar additionally forms larger flowers than the Charade cultivar. It further has been observed that the new cultivar can exhibit light yellow variegation in the foliage when grown under high light conditions (>5,000 foot candles).

When plant material of the BSR-195 Salmon cultivar is subjected to standard random amplified polymorphic DNA marker analysis (RAPD) using polymerase chain reaction (PCR) and a known unique set of DNA primers, it is found to exhibit a different fingerprint map when compared to that of the Charade cultivar which confirms its genetic distinctiveness.

Plants of the new cultivar will be marketed under the Celebration trademark by George J. Ball, Inc.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at West Chicago, Ill., U.S.A.

DETAILED DESCRIPTION

The chart used in the identification of colors described herein is The R.H.S. Colour Chart of The Royal Horticultural Society, London, England, The color values were determined at West Chicago, Ill., U.S.A. during the first week of April, 1993. The plants were produced from cuttings taken from stock plants and were grown under standard greenhouse conditions comparable to those used in commercial practice while utilizing a soilless growth medium and maintaining temperatures of approximately 72° F. during the day and approximately 65° F. during the night.

Propagation:

*Type cutting.*—Terminal tip.

*Time to initiate roots.*—Approximately 14 to 21 days with the shorter times generally being experienced in the summer and the longer times in the winter.

*Rooting habit.*—Fibrous and branching.

Plant Description:

*Form.*—Basal branching.

*Habit of growth.*—Upright mounded. A mature plant commonly measures approximately 13 to 14 cm. in height and approximately 19 to 20 cm. in width when grown in the greenhouse, and when grown in the field approximately 23 to 25 cm. in height and approximately 37 to 40 cm. in width. This can be compared to the Charade cultivar that commonly measures approximately 10 to 12 cm. in height and approximately 17 to 19 cm. in width when grown in the greenhouse, and when grown in the field approximately 19 to 20 cm. in height and approximately 35 to 40 cm. in width.

*Foliage.*—The configuration is narrow and lanceolate. The leaves of the BSR-195 Salmon cultivar measure approximately 8.0 cm×3.3 cm. while those of the Charade cultivar measure approximately 8.5 cm.×2.7 cm. The foliage of the BSR-195 Salmon cultivar is medium green, Green Group 138B with veins of Green Group 138A (abaxial) and Green Group 139A (adaxial). This can be compared to Greyed-Purple Group 187B (abaxial) and Green Group 139A with veins of Red Group 53B (adaxial) for the Charade cultivar. Under higher light conditions the foliage of the BSR-195 Salmon cultivar is Green Group 139A at the margins and yellow group 7A central variegation. The stem color of BSR-195 Salmon cultivar is Yellow-Green Group 144D, while that of the Charade cultivar is Red-Purple Group 59A.

Flower description:

*Flowering habit.*—Freely flowering.

*Natural flowering season.*—Year-round in greenhouse environment.

*Flowers borne.*—Above foliage, arising from leaf axils.

*Flower color.*—Red Group 50B (abaxial) and Red Group 50A (adaxial). This can be compared to Red Group 43C (abaxial) and Red Group 43B (adaxial) for the Charade cultivar.

*Quantity of flowers.*—Approximately 8 to 10 per stem.

*Number of petals.*—Five.

*Flower diameter.*—Approximately 6.7 cm. which can be compared to approximately 6.0 cm. for the Charade cultivar.

*Nectary length.*—Approximately 40 cm. which can be compared to approximately 5.5 cm. for the Charade cultivar.

*Nectary color.*—Red Group 53C which can be compared to Red Group 46C for the Charade cultivar.

*Reproductive organs.*—The anthers are fused together forming one organ that surrounds the pistil. Generally, the anthers shed pollen prior to the stigma becoming receptive. The pollen color is Yellow-Green Group 3C compared to Yellow-Orange Group 20C for the Charade cultivar. The stigma color is Green-White Group 157B and can be compared to Red Group 46C exhibited by the Charade cultivar. The ovary color is Yellow-Green Group 144A and can be compared to Red-Purple Group 59A exhibited by the Charade cultivar.

I claim:

1. A new and distinct cultivar of New Guinea Impatiens named BSR-195 Salmon, substantially as herein shown and described, which:

(a) exhibits attractive large salmon blosoms, (b) exhibits a good basal branching character, (c) exhibits an upright mounded growth habit, and (d) exhibits slightly variegated foliage under high light conditions.

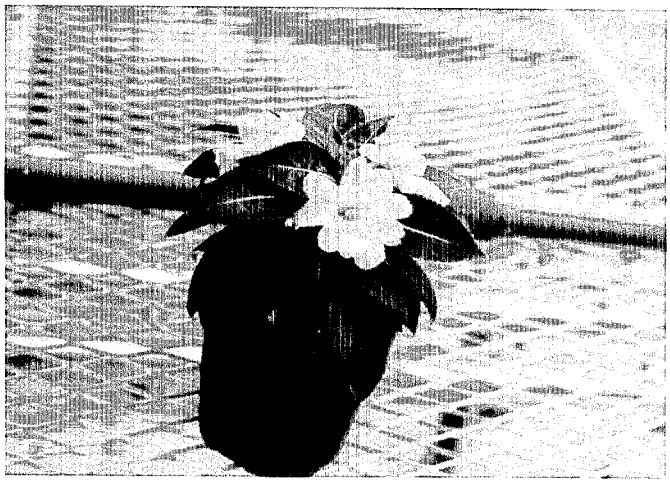

* * * * *